United States Patent [19]

Catsimpoolas

[11] Patent Number: 4,500,524

[45] Date of Patent: Feb. 19, 1985

[54] TRANQUILIZING AND REDUCING OR PREVENTING SEIZURES

[75] Inventor: Nicholas Catsimpoolas, Newton Centre, Mass.

[73] Assignee: Trustees of Boston University, Boston, Mass.

[21] Appl. No.: 522,134

[22] Filed: Aug. 11, 1983

Related U.S. Application Data

[63] Continuation-in-part of Ser. No. 418,240, Sep. 15, 1982, abandoned.

[51] Int. Cl.³ .................... A61K 31/33; A61K 31/525
[52] U.S. Cl. .................................... 514/250; 514/251
[58] Field of Search ............................... 424/252, 244

[56] References Cited

PUBLICATIONS

Merck Index, 9th Ed., (1976), pp. 543–544 and 1064–1065.

Primary Examiner—Stanley J. Friedman
Attorney, Agent, or Firm—Paul J. Cook; Lawrence Gilbert

[57] ABSTRACT

Seizures are inhibited or prevented and tranquilizing effect induced by administering riboflavin or a riboflavin analog, alone or in combination with a conventional anticonvulsant or tranquilizer to enhance its effect.

6 Claims, 8 Drawing Figures

Figure 1:
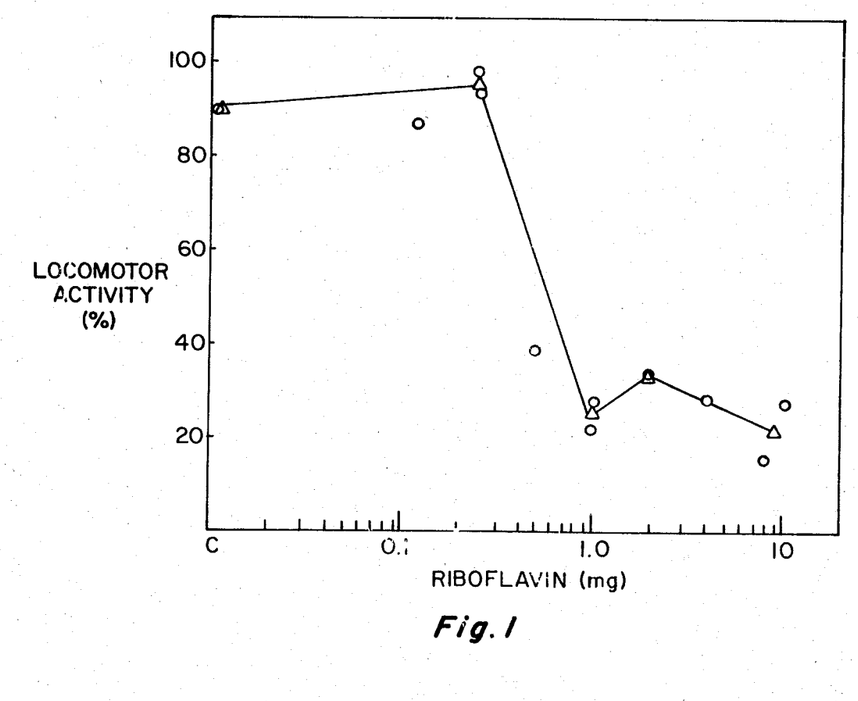
Figure 2:
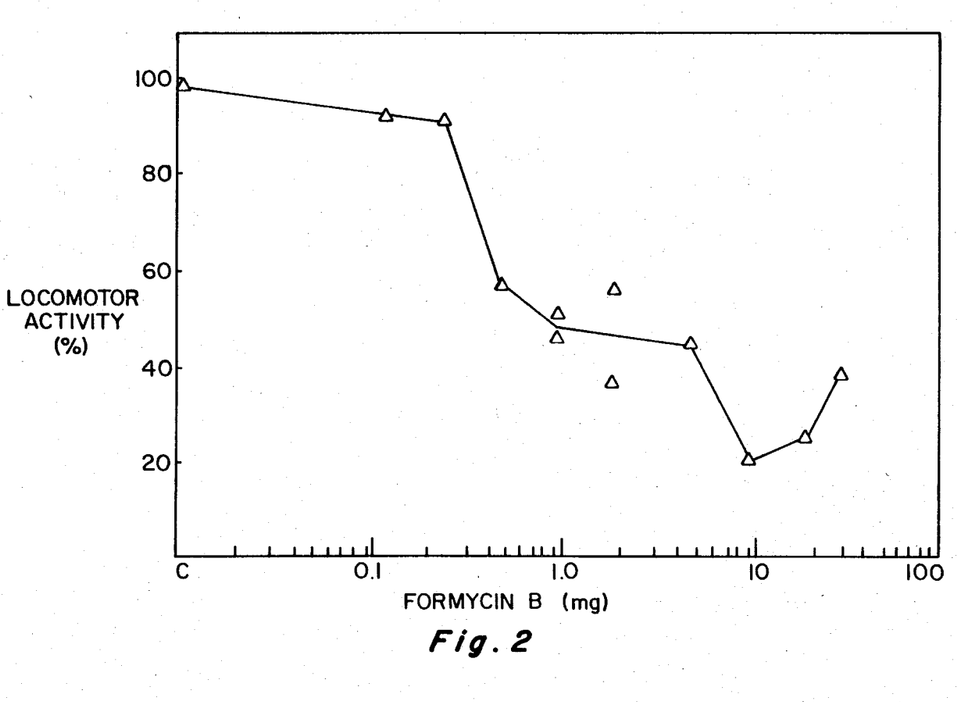
Figure 3:
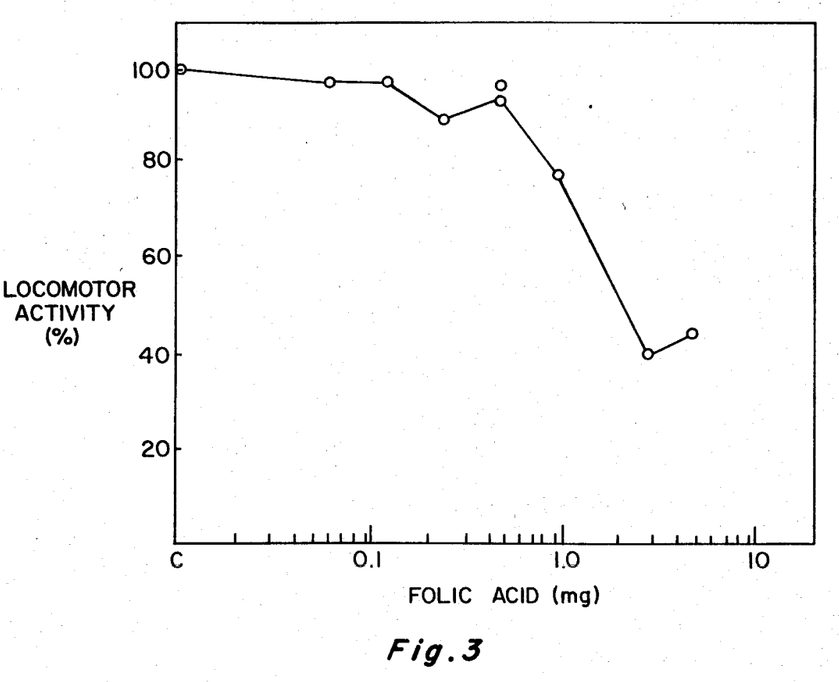
Figure 4:
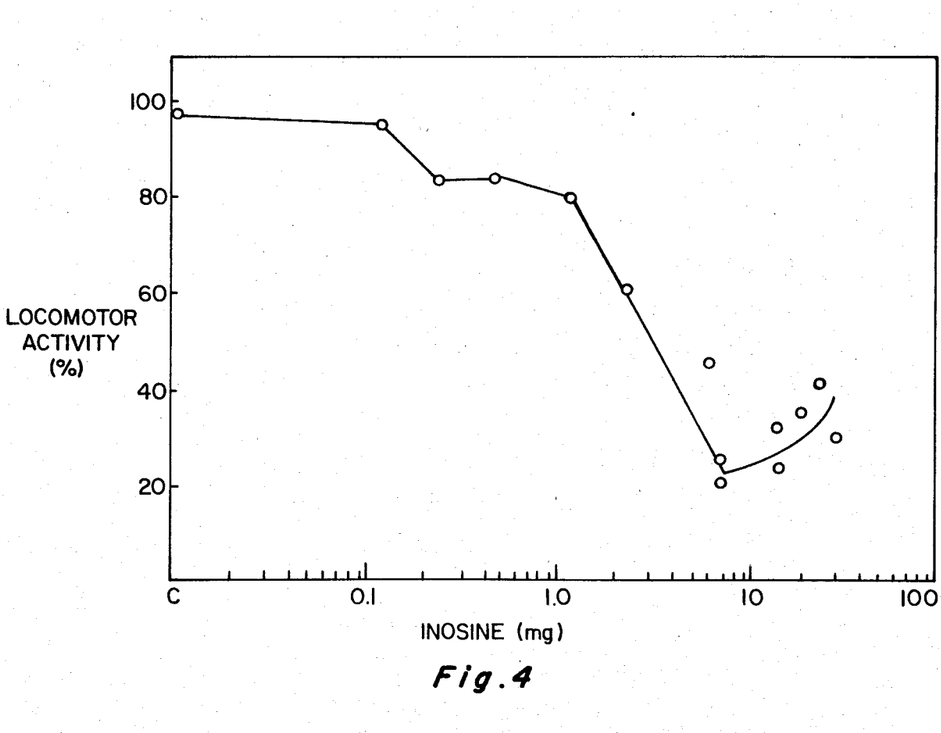
Figure 5:
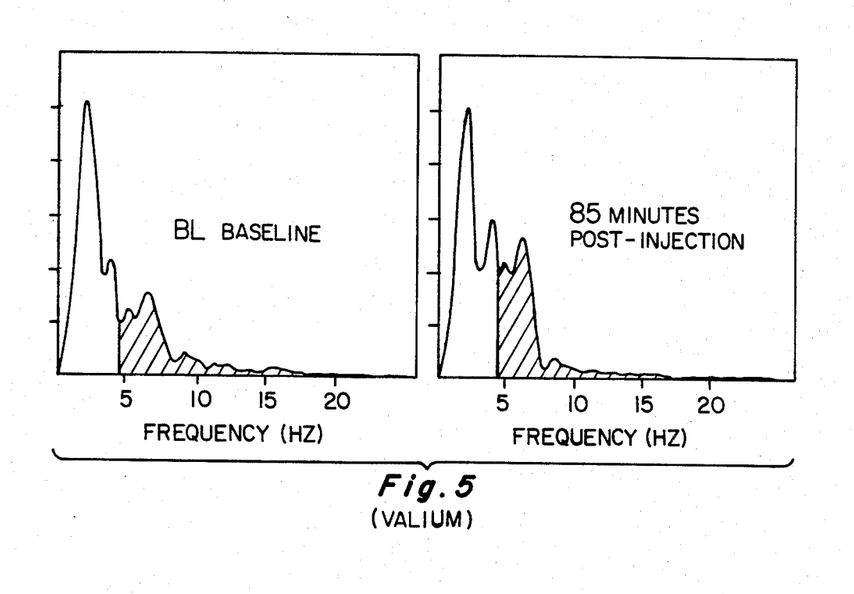

Fig. 5
(VALIUM)

Figure 6:
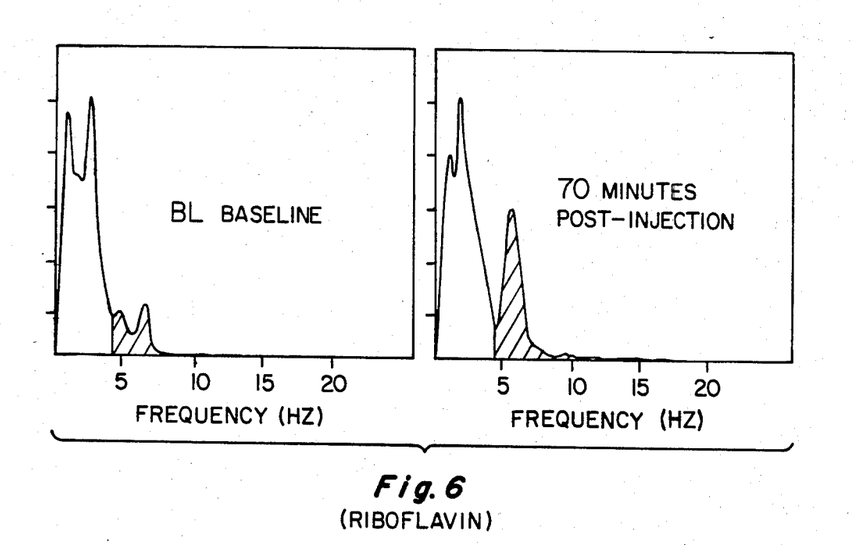

Fig. 6
(RIBOFLAVIN)

THE TIME COURSE OF PNP INHIBITION IN
THE ABSENCE (●) AND PRESENCE (○) OF
90 μg/ml RIBOFLAVIN AT 37°C

Figure 7:
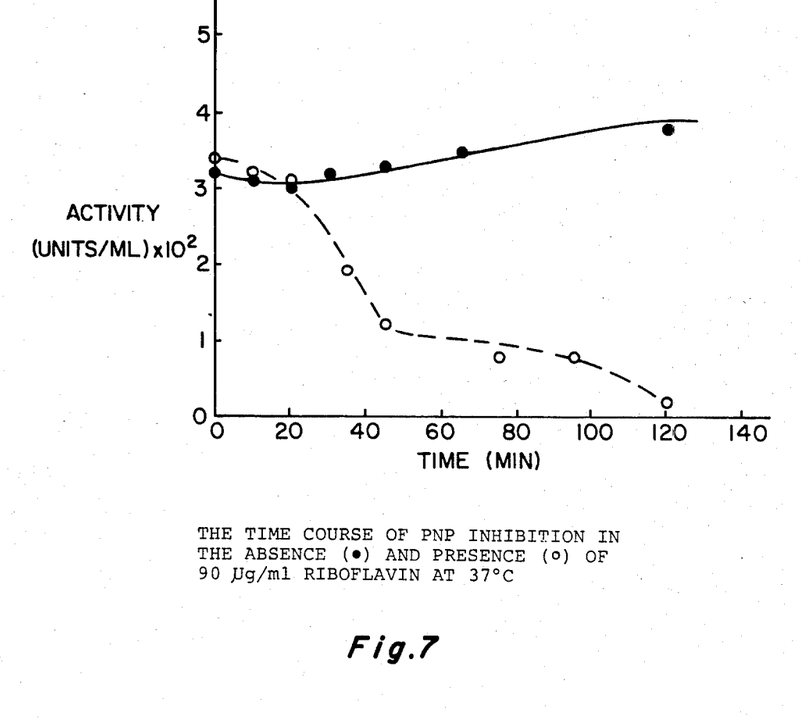
Figure 8:
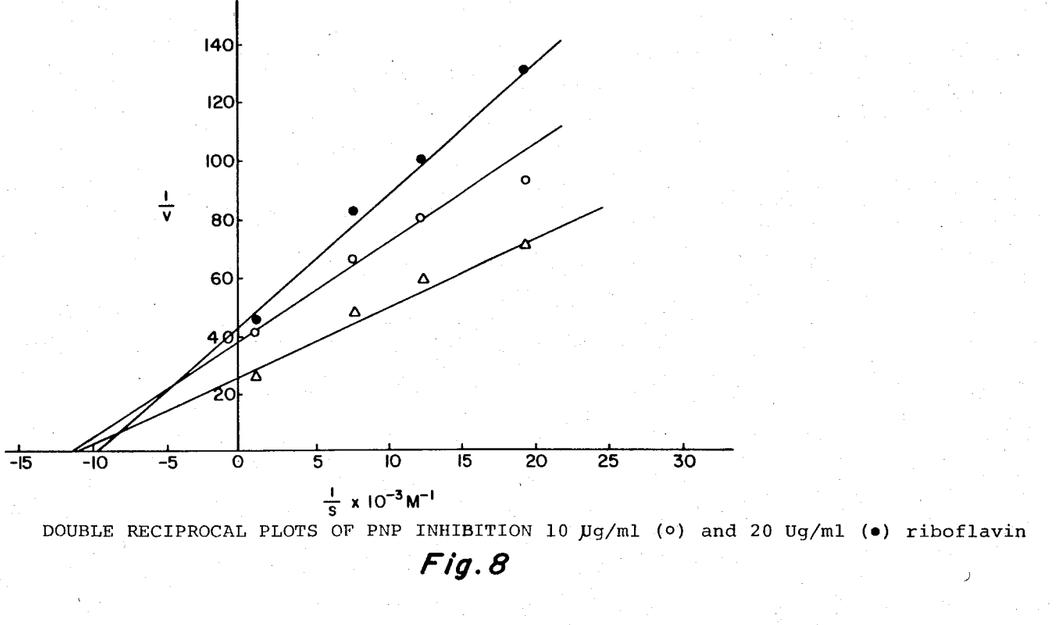

*Fig.7*

TRANQUILIZING AND REDUCING OR PREVENTING SEIZURES

REFERENCE TO RELATED APPLICATION

This application is a continuation-in-part of application Ser. No. 418,240, filed Sept. 15, 1982, now abandoned.

FIELD OF THE INVENTION

The invention relates to a method for controlling seizures or inducing a tranquilizing effect by administering to a patient riboflavin or a riboflavin analog.

BACKGROUND OF THE INVENTION

The functioning of the central nervous system (CNS), including the brain, is highly dependent on a variety of receptor sites which show more or less specific binding capacity for a variety of natural (endogenous) chemical entities. The actions of some drugs (foreign chemical substances) relate to their capacity to bind to such specific receptors, thus either triggering or blocking the actions influenced by the receptors. The existence of some brain receptors first came to be detected by the discovery that certain active drugs bind to them. Consequently, such receptors may be named after the drug involved, for example, morphine receptors or benzodiazepine receptors. The scientist then seeks to learn the nature of the endogenous (natural) substance in the brain which react with these receptors to better understand the normal function of the receptor, and its role in disease and the action of relevant drugs.

Thus, benzodiazepiine receptors are naturally occurring binding sites found within the CNS generally in all animals, including man. These receptors directly influence an animal's behavioral characteristics. They are called benzodiazepine receptors because one broad class of pharmacologically active compounds able to bind to them, are collectively of the chemical structure known as benzodiazepines. Agents which bind to these receptors are able to directly influence, modify or control in varying degrees the neurological and behavioral patterns of mammals.

The benzodiazepines and benzodiazepine-like compositions are often used as drugs for a wide variety of neuropsychiatric conditions of man, but their most popular use is in the treatment of anxiety. The full range of pharmacological effects caused by the binding of these pharmacologically active compositions to the benzodiazepine receptors in the central nervous system includes anticonvulsant, muscle relaxant, anxiolytic and sedative properties, and the effect in animals can be correlated directly with such activity in man. For more specific details, see Tallman, Paul, Skolnick and Gallager, *Science*, 207:274 (1980); Greenblatt and Schder, *Benzodiazepine in Clinical Practice*, (1974); Garattine, Mussiri and Randall, *The Benzodiazepines* (1973); and Zoinden and Randall, *Advanced Pharmacology*, 5:213 (1967).

According to a recent conservative estimate, at least 8,000 tons of benzodiazepines are consumed each year in the United States alone. This estimate, however, is based only upon the consumption of chlordiazepoxide (Librium), diazepam (Valium) and flurazepam (Dalmane). The widespread use and abuse, intentionally or accidentally, of benzodiazepines and benzodiazepine-like drugs with their concomitant risk of seizures and other adverse reactions due to excessive dosage or withdrawal reactions, have drawn attention to the need for and importance of identifying the natural biochemically and pharmacologically active ligands which may be modulators and able to influence the receptor involved in the action of the benzodiazepine.

Until recently, little was known about the identity of the endogenous (natural) ligand(s) which interact with the so-called benzodiazepine receptor. Generally, the therapeutic use of an endogenous ligand normally found in the central nervous system which influences a given receptor is preferred to a foreign synthetic chemical. Such naturally occurring agents are less likely to cause drug-induced side effects, either by direct action or as a result of withdrawal.

Some studies have suggested that the purine nucleosides inosine, 2-deoxyinosine and 2-deoxyguanosine may act as endogenous ligands and, therefore, as modulators of the benzodiazepine receptors in the central nervous system (See *Life Science*, 24:851 (1979); *Science*, p. 727 (1981); *Proc. Natl. Acad. Sci.*, 74:3805 (1977); and *Science*, 198:849 (1977). Inosine, in particular, is recognized as a benzodiazepine antagonist: it is able to antogonize the gamma aminobutyric acidmimetic action of diazepam in vivo, antagonize pentylenetetrazole-induced seizures, and reverse diazepam-induced stimulation of mouse exploratory behavior (See *Life Science*, 25:1963 (1979); and *Proc. Natl. Acad.*, 76:1515 (1979). A major difficulty, however, is that inosine in vivo is a substrate for the enzyme purine nucleoside phosphorylase (PNP) which also is found normally in brain tissue. Increased concentrations of inosine are difficult to achieve because of the action of this enzyme within the CNS. Consequently, the utility of inosine itself as a therapeutic agent is very limited, even if it did reach the brain. The other purine nucleosides are similarly limited in various respects unless PNP is blocked.

Accordingly, insofar as is presently known, no endogenous modulating ligand has been isolated which can be maintained in the CNS in sufficiently high concentration to serve as a substitute for or modulator of benzodiazepine and benzodiazepine-like composition to reduce or entirely prevent the severity and frequency of seizures, whether induced by drugs, indigenously or by other factors.

SUMMARY OF THE INVENTION

A method for tranquilizing and/or inhibiting seizures in a patient is provided which comprises administration of a predetermined quantity of riboflavin, or a riboflavin analog selected from the group consisting of formycin B, folic acid, 8-aminoguanosine, D, L-6-methyl 5,6,7,8 tetrahydropterine, and allopurinol riboside related PNP inhibitors or the like. The riboflavin or riboflavin analog can be administered either alone or concomitantly with conventional sedatives, tranquilizers or anticonvulsants.

DETAILED DESCRIPTION OF THE INVENTION

In accordance with this invention, it has been found that a naturally occurring essential nutrient, riboflavin, and analogs, have benzodiazepine-like, and benzodiazepine potentiating properties, and can be used in combination with other anxiolytic and anticonvulsant agents to enhance their efficacy and safety. A possible mechanism to explain the action of the riboflavin group is their capacity to inhibit the enzyme purine nucleoside phosphorylase (PNP), resulting in elevated levels of endogenous agonists of the benzodiazepine receptor.

Riboflavin (Vitamin $B_2$) is a well-known essential nutrient with a normal daily requirement of about 1 or 2 mg (about 0.01–0.05 mg/kg). There has been no evidence or suggestions that it has utility as an anticonvulsant or tranquilizing agent when used in larger but still well tolerated doses.

The present invention comprises the administration of riboflavin or an appropriate riboflavin analog (hereinafter, "inhibitor") to a patient or animal to tranquilize, sedate and/or prevent seizures. The presumed mechanism of action is the accumulation of active endogenous ligands in the CNS by inhibiting the enzyme PNP. The inhibitor may be introduced into the body orally, rectally or by injection. The described doses of inhibitor are sufficient to achieve brain levels which inhibit. In the case of riboflavin, its effective dose range to achieve the necessary concentration in CNS is from about 0.1 mg/kg of body weight up to about 50 mg/kg, preferably from about 5 mg/kg to 15 mg/kg.

In accordance with this invention, the riboflavin or riboflavin analog can be administered either alone or in combination with known anticonvulsants such as the benzodiazepines (ex: chlordiazepoxide, diazepam), the barbiturates (ex: primedon, phenobarbital), phenytoin or tegratol. The known anticonvulsant can be administered at the normal dosage or at a dosage lower than the normal dosage down to about 10% of the normal dosage. The riboflavin or analog can also be administered together with a preparation of an endogenous agonist such as inosine or a precursor selected for its ability to cross the bloodbrain barrier.

Riboflavin is a well-known and defined biochemical composition which is present endogenously within the CNS. Riboflavin deficiency in man is known to result in mental depression and muscle spasticity. It has now been demonstrated that riboflavin is a non-competitive inhibitor of the enzyme purine nucleoside phosphorylase (PNP) which metabolizes inosine endogenously. Preincubation of PNP with riboflavin inhibits its activity. Folic acid and formycin B are known examples of competitive inhibitors of PNP. These compositions were tested for their effects in models of seizures and behavior and were discovered to be anticonvulsant and tranquilizing.

The data presented in the examples show that riboflavin and these analogous inhibitors of PNP (1) cause a dose-related reduction in locomotor activity characteristic of tranquilizers and sedatives,
(2) have electroencephalographic effects similar to the benzodiazepine tranquilizer diazepam (Valium),
(3) block or delay Metrazol-induced seizures,
(4) potentiate the protective (anticonvulsant) effect of known effective antiepileptic agents such as Valium and Dilantin (phenytoin) against Metrazol-induced seizures.

Doses of riboflavin readily tolerated in man can have the previously unrecognized capacity to inhibit convulsions and to tranquilize. In combination with these and other effective agents, riboflavin may be significantly active in even lower doses. Based on calculations of known animal/human potency ratios in the relevant pharmacologic areas, and the potency of riboflavin and analogs now discovered in animal models, the following ratio and dose limits and utility examples are presented:

1. For use as single entity therapy in mammals to control or prevent seizures or to tranquilize.
   a. Riboflavin in doses of 0.1 to 50 mg/kg, preferably 10 mg/kg.
   b. Riboflavin analogs/inhibitors of PNP such as folic acid, 8 amino guanosine or formycin B in doses up to their known safe limits in man.
2. For use in combination with other active agents to achieve a greater effect than is achievable with either agent alone in adequately safe and tolerated doses. For example:
   a. In combination with dilantin to prevent or control seizures in a milligram dose ratio of from 1:1 to 1:50 (dilantin to riboflavin), preferably about 1:15.
   b. In combination with a benzodiazepine such as valium to tranquilize or to prevent or control seizures in a ratio of from 1:10 (valium to riboflavin) to 1:1000, preferably about 1:250.

The above may be formulated for oral administration (tablets, capsules, solutions, suspension, etc.) as suppositories for rectal administration, or for parenteral injection in sterile formulations such as in the following examples:

| DOSAGE UNITS (ex: Tablets or Capsules) | | |
|---|---|---|
| Example # | Riboflavin mg | |
| | | Diazepam mg |
| I | 10 | 10 |
| II | 100 | 5 |
| III | 1000 | 1 |
| | | Phenytoin ml |
| IV | 10 | 100 |
| V | 100 | 50 |
| VI | 1000 | 10 |
| | | Inosine mg |
| VII | 10 | 1000 |
| VIII | 100 | 100 |
| IX | 1000 | 10 |
| | | Tegratol mg (Carbamazepine) |
| X | 10 | 200 |
| XI | 100 | 10 |
| | | Phenobarbital mg |
| XXI | 10 | 100 |
| XIV | 100 | 50 |
| XV | 1000 | 10 |

| PREPARATION FOR INJECTION Sterile Ampoules of Dry: | | |
|---|---|---|
| Riboflavin mg | plus | Sodium anobarbital mg |
| 20 | | 250 |
| 100 | | 125 |
| 1000 | | 25 |

| Sterile Solutions of: | | |
|---|---|---|
| Riboflavin mg/ml | plus | Diazepam mg/ml |
| 20 | | 10 |
| 100 | | 5 |
| 1000 | | 1 |
| Folic Acid | plus | Phenytoin |
| 20 | | 100 |
| 100 | | 50 |
| 1000 | | 10 |

Dosage units combining more than 2 active ingredients may also be formulated, for example:

100 mg Riboflavin—Phenytoin 100 mg—Phenobarbital 15 mg

Riboflavin and analogs may be competitive/reversible or non-competitive/"irreversible" in their inhibition of the PNP enzyme. Either type of inhibition is consistent with the utility described in this application, although non-competitive inhibition is likely to be clinically preferable in giving smoother and longer lasting action. On this basis riboflavin itself may be the preferred agent for practicing this invention. Riboflavin is also a safer agent based on empirical experience as documented, for example, in the standard reference text, "AMA Drug Evaluations", 5th ed., 1983. On page 1138, it states: "There is no acceptable evidence that riboflavin has any effect other than in the treatment or prevention of its riboflavin deficiency state. No toxic effects have been reported clinically."

Consistent with a lack of riboflavin toxicity is its general availability in "health stores" in vitamin preparations containing 100 mg of riboflavin per tablet (50 times the recommended daily dose as a vitamin). In contrast, the dosage of folic acid, for example, is limited by known toxic potential.

The following examples illustrate the present invention and are not intended to limit the same.

EXAMPLE I

Effect on Locomotor Activity in the Mouse

Locomotor activity is a non-specific but significant behavioral test. It is characteristic of sedatives and tranquilizers that they reduce locomotor activity in a dose-related manner. FIGS. 1–4 show a dose dependent reduction of locomotor activity after intraperitoneal administration of riboflavin, formycin B, folic acid or inosine into mice. The duration of the test was preset at 10 minutes, but the effects were observed to last for much longer periods of time. Varying amounts of these compounds ranging from 0.1 to 50.0 mg (equivalent to 3.3–1665 mg/kg) in Gey's Balance Salt Solution (GBSS) were injected intraperitoneally (I.P.) and the activity was marked on an event recorder. Locomotor activity was taken to include walking, climbing, jumping and digging. The salt solution alone had no effect on locomotor activity and the results with these control groups were consistent from study to study. A comparison of the data in FIGS. 1–4 shows a great similarity in the statistically significant dose-response curves of the four compounds tested, suggesting a similar site of action.

The intensity of mouse exploratory activity has been shown to correlate significantly with more intricate animal anxiety models, and inosine reversed the stimulation of mouse exploratory activity induced by high doses of diazepam [See Crawley et al, *Science*, 211:725 (1981)]. The dose range at which each of these inhibitors had an effect on the locomotor activity in our studies was similar to that observed for the inosine reversal of the diazepam increase in mouse exploratory behavior.

EXAMPLE II

Effect of EEG Power Spectrum

It is well established in animals and man than CNS active drugs alter the frequency of occurrence of electroencephalographic (EEG) waves of various types, and that these types of alteration can be characteristic of the type of CNS active drug administered [Fink, M. et al, Pharmacopsychiatry, 12:35 (1979)].

FIGS. 5 and 6 illustrate the similarity of the change induced on the EEG power spectrum in rats given either valium or riboflavin, reinforcing the claimed similarity in the CNS effects of these two agents. Both agents caused a marked increase in waves with a frequency of 4 to 8 HZ.

EXAMPLE III

Effect of PNP Inhibitors on Metrazol-Induced Seizures in Mice

Adult male outbred mice approximately 2 months of age with an average weight of 30 grams were injected intraperitoneally with varying doses as shown in Table I or riboflavin, formycin B and folic acid in 0.5 ml of GBSS. After 30 minutes of elapsed time, each animal was again injected intraperitoneally this time with a 120 mg/kg of Metrazol, a dose which is quickly convulsive and 95% lethal. The results shown in Table I indicate that all 3 agents have inhibitory properties in that seizure latency was significantly extended even though death following this dose of Metrazol was not prevented by formycin B or folic acid. With riboflavin in the doses of 9 to 15 mg, some of the animals survived, and the optimal (9 mg) dose level in particular prevented seizures entirely in 50% of the test animals. The extended latency periods reflect the protective effects of these doses as well.

In another experiment, another PNP inhibitor, 8-aminoguanosine was studied to determine its effect on Metrazol-induced seizures. The 8-aminoguanosine was administered as pretreatment at a concentration of 10 mg/ml in GBSS while Metrazol was subsequently administered at a concentration of 10 mg/ml GBSS (0.36 ml/mouse). The results shown in Table II strongly resemble those previously presented for other PNP inhibitors in Table I.

Another experiment with riboflavin evaluated the effect of a shorter vs longer pretreatment interval. Mice were again injected I.P. with a 15 mg dose of riboflavin in 0.5 ml of GBSS, and challenged after 7 or 30 minutes with 3.5 mg of Metrozol in 0.36 nl GBSS I.P. The results in Table III show that with a 7 minute interval, there is a doubling of the latency period compared to control mice, while with a 30 minute interval, the seizure latency period was even greater, and 3 of the 7 mice survived the procedure. These data indicate that more than 7 minutes is necessary for optimal riboflavin action, even though absorption form the peritoneum is characteristically very rapid and complete. This fact is consistent with the proposed mechanism of action of riboflavin, i.e., the central effect of PNP inhibitor may not be fully evident until an adequate period of time after administration. While this is important in acute studies, in maintenance therapy riboflavin can be continuously effective in keeping PNP inhibited. Endogenous agonist levels will remain elevated, preventing epileptic seizures.

The above data also indicate that there is an optimal dose range, and that massive doses of these agents, like excessive doses of the benzodiazepines, can have a dampening or reverse effect from optimal therapeutic doses.

TABLE I

| Effect of Pretreatment on Response to Metrazol | | | |
|---|---|---|---|
| Drug | Dose mg/mouse | Seizure Latency (min) | % Without Seizure | % Surviving |
| None | — | 1.02 ± 0.02 | 0 | 0 |

TABLE I-continued

Effect of Pretreatment on Response to Metrazol

| Drug | Dose mg/mouse | Seizure Latency (min) | % Without Seizure | % Surviving |
|---|---|---|---|---|
| Formycin B | 12 | 3.01 ± 2.00 | 0 | 0 |
|  | 15 | 1.68 ± 0.37 | 0 | 0 |
| Folic Acid | 12 | 2.20 ± 0.28 | 0 | 0 |
| Riboflavin | 6 | 1.61 ± 0.26 | 0 | 25 |
|  | 9 | 4.20 ± 1.56 | 0 | 50 |
|  | 12 | 5.04 ± 4.97 | 50 | 50 |
|  | 15 | 1.74 ± 1.04 | 7 | 0 |

TABLE II

Effect of Pretreatment with 8-Aminoguanosine on Response to Metrazol (120 mg/kg i.p. 30 minutes later)

| Mouse No. | 8-Aminoguanosine (mg/mouse) | Seizure Latency (min) |
|---|---|---|
| 1 | 3 | 1.67 |
| 2 | 3 | 1.13 |
| 3 | 3 | 1.16 |
| 4 | 3 | 5.16 |
|  |  | 2.28 ± 1.67 |
| 5 | 9 | 5.70 |
| 6 | 9 | 9.09 |
| 7 | 9 | 8.68 |
| 8 | 9 | 4.04 |
|  |  | 6.89 ± 2.08 |
| 9 | 15 | 2.67 |
| 10 | 15 | 1.58 |
| 11 | 15 | 1.08 |
| 12 | 15 | 2.74 |
|  |  | 2.08 ± 0.71 |
| 13 | 0 | 0.91 |
| 14 | 0 | 1.05 |
| 15 | 0 | 0.81 |
| 16 | 0 | 1.00 |
|  |  | 0.94 ± 0.09 |

TABLE III

Effect of Time Interval Between Pretreatment and Challenge on The Protective Effect of Riboflavin Against Metrazol Seizures

|  | Onset of Seizures (min) | Death (min) |
|---|---|---|
| (No Riboflavin) |  |  |
| #1 | 0.77 | 5.80 |
| 2 | 1.33 | 10.50 |
| 3 | 0.93 | 7.40 |
| 4 | 0.65 | 4.10 |
| 5 | 1.54 | 4.00 |
| 6 | 1.30 | 3.60 |
| 7 | 1.50 | 8.80 |
|  | 1.15 ± 0.33 | 6.31 ± 2.47 |
| Preinjected with 15 mg Riboflavin (i.p.) 7 min before PTZ challenge |  |  |
| #1 | 1.20 | 16.00 |
| 2 | 1.50 | 5.80 |
| 3 | 1.30 | 8.77 |
| 4 | 5.40 | 15.64 |
| 5 | 3.87 | 27.76 |
| 6 | 1.47 | 6.25 |
| 7 | 1.40 | 12.60 |
|  | 2.30 ± 1.53 | 13.26 ± 7.06 |
| Preinjected with 15 mg Riboflavin (i.p.) 30 min before PTZ challenge |  |  |
| #1 | 2.33 | * |
| 2 | 2.36 | 4.70 |
| 3 | 2.98 | * |
| 4 | 3.37 | 23.23 |
| 5 | 1.31 | 6.50 |
| 6 | 6.95 | * |
| 7 | 1.65 | 7.90 |

TABLE III-continued

Effect of Time Interval Between Pretreatment and Challenge on The Protective Effect of Riboflavin Against Metrazol Seizures

| Onset of Seizures (min) | Death (min) |
|---|---|
| 2.99 ± 1.74 | — |

*Survivors

EXAMPLE IV

Combined Effect of Riboflavin and Valium on Metrazol Seizures

Following the test procedures described above, mice were challenged with Metrazol after pretreatment with valium, riboflavin or a combination of riboflavin and valium in GBSS. The Metrazol was administered at a concentration of 10 mg/ml GBSS and at a 0.36 ml/mouse. The valium (30 μg/mouse) was administered at a concentration of 0.5 mg/ml in 50% propylene glycol-50% GBSS. The riboflavin (12 mg in 0.4 ml) was administered at a concentration of 30 mg/ml GBSS. The results are shown in Table IV. The combined treatment had a greater effect on latency than either agent alone.

The data in Table IV also demonstrate the greater effect of Dilantin (phenytoin) plus riboflavin over either drug alone as was found with the riboflavin/valium combination.

TABLE IV

Effect of Pretreatment with Inactive vs Active Agents, Alone and in Combinations, on Metrazol Seizures

| Sample | Seizure Latency (min) |
|---|---|
| Control (400 μl GBSS) | 0.91 |
| Control (400 μl GBSS) | 0.81 |
| Control (400 μl GBSS) | 1.05 |
| Control (400 μl GBSS) | 1.00 |
|  | 0.94 ± 0.09 |
| Talcum Powder (15 mg/mouse) | 0.53 |
| Talcum Powder (15 mg/mouse) | 0.90 |
| Talcum Powder (15 mg/mouse) | 1.05 |
| Talcum Powder (15 mg/mouse) | 1.35 |
|  | 0.95 ± 0.29 |
| Talcum Powder (9 mg/mouse) | 0.78 |
| Talcum Powder (9 mg/mouse) | 1.21 |
| Talcum Powder (9 mg/mouse) | 0.45 |
|  | 0.81 ± 0.31 |
| Riboflavin (12 mg/mouse) | 1.79 |
| Riboflavin (12 mg/mouse) | 1.43 |
| Riboflavin (12 mg/mouse) | 1.23 |
| Riboflavin (12 mg/mouse) | 2.10 |
| Riboflavin (12 mg/mouse) | 2.29 |
| Riboflavin (12 mg/mouse) | 1.77 |
| Riboflavin (12 mg/mouse) | 2.07 |
| Riboflavin (12 mg/mouse) | 1.51 |
| Riboflavin (12 mg/mouse) | 4.03 |
| Riboflavin (12 mg/mouse) | 1.69 |
|  | 1.99 ± 0.74 |
| Valium (30 ug/mouse) | 0.97 |
| Valium (30 ug/mouse) | 2.61 |
| Valium (30 ug/mouse) | 3.25 |
|  | 2.93 ± 0.32 |
| Valium (30 ug) + Riboflavin (12 mg/mouse) | 2.31 |
| Valium (30 ug) + Riboflavin (12 mg/mouse) | 7.17 |
| Valium (30 ug) + Riboflavin (12 mg/mouse) | 4.13 |
| Valium (30 ug) + Riboflavin (12 mg/mouse) | 3.65 |
| Valium (30 ug) + Riboflavin (12 mg/mouse) | 1.64 |
|  | 3.78 ± 1.91 |
| Dilantin (0.9 mg/mouse) | 0.75 |
| Dilantin (0.9 mg/mouse) | 1.54 |
| Dilantin (0.9 mg/mouse) | 0.91 |
| Dilantin (0.9 mg/mouse) | 1.94 |
| Dilantin (0.9 mg/mouse) | 0.78 |
|  | 1.18 ± 0.47 |

TABLE IV-continued

Effect of Pretreatment with Inactive vs Active Agents, Alone and in Combinations, on Metrazol Seizures

| Sample | Seizure Latency (min) |
|---|---|
| Dilantin (0.9 mg) + Riboflavin (12 mg)/mouse | 1.37 |
| Dilantin (0.9 mg) + Riboflavin (12 mg)/mouse | 4.25 |
| Dilantin (0.9 mg) + Riboflavin (12 mg)/mouse | 1.32 |
|  | 2.31 ± 1.36 |
| Dilantin (3 mg/mouse) | 2.31 |
| Dilantin (3 mg/mouse) | 2.23 |
|  | 2.27 ± 0.04 |
| Dilantin (3 mg) + Riboflavin (12 mg)/mouse* | 3.84 |
| Dilantin (3 mg) + Riboflavin (12 mg)/mouse* | 4.54 |
| Dilantin (3 mg) + Riboflavin (12 mg)/mouse* | ** |
|  | >3.84 ± 0.70 |

*Combined in one dose
**No seizure

I claim:

1. A method for inhibiting convulsions in an animal caused by abnormalities of the benzodiazepine receptors in the central nervous system of the animal or tranquillizing an animal which comprises introducing an inhibitor selected from the group consisting of riboflavin and folic acid into the central nervous system of said animal in an amount to inhibit convulsions or to tranquillize said animal.

2. The mehtod of claim 1 wherein the inhibitor is riboflavin.

3. The method of claim 1 wherein the inhibitor is folic acid.

4. The method of any one of claims 1, 2 or 3 wherein said inhibitor is introduced into the central nervous system of an animal at least about 5 minutes prior to the administration of a seizure-inducing composition.

5. A composition of matter comprising (a) riboflavin or folic acid and (b) diazepam in a weight ratio of between about 2:1 and 1000:1 wherein the total milligram dose is between about 10 and 1000 mg.

6. A composition of matter comprising (a) riboflavin or folic acid and (b) a benzodiazepine in a weight ratio of between about 2:1 and 1000:1 wherein the total milligram dose is between about 10 and 1000 mg.

* * * * *